(12) United States Patent
Baril (10) Patent No.: US 10,542,970 B2
(45) Date of Patent: Jan. 28, 2020

(54) ENDOSCOPIC STITCHING DEVICE (71) Applicant: Covidien LP, Mansfield, MA (US)

(72) Inventor: Jacob Baril, White Plains, NY (US)

(73) Assignee: COVIDIEN LP, Mansfield, MA (US)

( * ) Notice: Subject to any disclaimer, the term of this patent is extended or adjusted under 35 U.S.C. 154(b) by 307 days.

(21) Appl. No.: 15/468,163

(22) Filed: Mar. 24, 2017

(65) Prior Publication Data
US 2017/0340320 A1 Nov. 30, 2017

Related U.S. Application Data (60) Provisional application No. 62/343,379, filed on May 31, 2016.

(51) Int. Cl.
A61B 17/04 (2006.01)
A61B 17/00 (2006.01)

(52) U.S. Cl.
CPC .... A61B 17/0469 (2013.01); A61B 17/00234 (2013.01); A61B 2017/047 (2013.01)

(58) Field of Classification Search
CPC ............ A61B 17/0625; A61B 17/0469; A61B 2017/047; A61B 2017/0609; A61B 2017/2913; A61B 2017/2915; A61B 2017/2916
See application file for complete search history.

(56) References Cited

U.S. PATENT DOCUMENTS 1,822,330 A 9/1931 Ainslie
2,327,353 A 8/1943 Karle
3,073,311 A 1/1963 Tibbs et al.
3,123,077 A 3/1964 Alcamo
3,687,138 A * 8/1972 Jarvik .............. A61B 17/12013
606/139
(Continued)

FOREIGN PATENT DOCUMENTS

DE 4423881 C1 10/1995
EP 0592244 A2 4/1994
(Continued)

OTHER PUBLICATIONS

European Search Report from EP 07 83 9340 dated Dec. 2, 2013 (8 pages).
(Continued)

Primary Examiner — Alexander J Orkin
(74) Attorney, Agent, or Firm — Carter, DeLuca & Farrell LLP (57) ABSTRACT An elongate shaft assembly for use with a stitching device includes a hub assembly and an end effector. The hub assembly includes insertion and engaging portions. The insertion portion includes a main rod, a rotatable hub operatively coupled with the main rod such that axial displacement of the main rod rotates the rotatable hub, and first and second arms operatively coupled with the rotatable hub such that rotation of the rotatable hub causes reciprocating axial displacement of the first and second arms. The engaging portion is movable relative to the insertion portion between a reload position in which the rotatable hub is in a distal-most position and rotatable independent of axial displacement of the main rod, and a loaded position in which axial displacement of the main rod rotates the rotatable hub.

22 Claims, 8 Drawing Sheets (56) References Cited

U.S. PATENT DOCUMENTS

| | | |
|---|---|---|
| 4,033,043 A * | 7/1977 | Cunningham ....... A61B 5/1076 |
| | | 33/806 |
| 4,236,470 A | 12/1980 | Stenson |
| 4,890,615 A | 1/1990 | Caspari et al. |
| 4,923,461 A | 5/1990 | Caspari et al. |
| 4,935,027 A | 6/1990 | Yoon |
| 5,037,433 A | 8/1991 | Wilk et al. |
| 5,042,707 A | 8/1991 | Taheri |
| 5,080,663 A | 1/1992 | Mills et al. |
| 5,100,421 A | 3/1992 | Christoudias |
| 5,100,430 A | 3/1992 | Avellanet et al. |
| 5,209,747 A | 5/1993 | Knoepfler |
| 5,271,543 A | 12/1993 | Grant et al. |
| 5,300,082 A | 4/1994 | Sharpe et al. |
| 5,308,353 A | 5/1994 | Beurrier |
| 5,314,445 A | 5/1994 | Heidmueller nee Degwitz et al. |
| 5,314,446 A | 5/1994 | Hunter et al. |
| 5,330,502 A | 7/1994 | Hassler et al. |
| 5,336,229 A | 8/1994 | Noda |
| 5,350,391 A | 9/1994 | Iacovelli |
| 5,358,498 A | 10/1994 | Shave |
| 5,374,277 A | 12/1994 | Hassler |
| 5,387,221 A | 2/1995 | Bisgaard |
| 5,389,103 A | 2/1995 | Melzer et al. |
| 5,391,176 A | 2/1995 | de la Torre |
| 5,403,342 A | 4/1995 | Tovey et al. |
| 5,405,352 A | 4/1995 | Weston |
| 5,439,478 A | 8/1995 | Palmer |
| 5,454,823 A | 10/1995 | Richardson et al. |
| 5,454,827 A | 10/1995 | Aust et al. |
| 5,472,446 A | 12/1995 | de la Torre |
| 5,478,344 A | 12/1995 | Stone et al. |
| 5,480,406 A | 1/1996 | Nolan et al. |
| 5,496,334 A | 3/1996 | Klundt et al. |
| 5,527,323 A | 6/1996 | Jervis et al. |
| 5,540,703 A | 7/1996 | Barker, Jr. et al. |
| 5,540,706 A | 7/1996 | Aust et al. |
| 5,549,617 A | 8/1996 | Green et al. |
| 5,549,637 A | 8/1996 | Crainich |
| 5,562,686 A | 10/1996 | Sauer et al. |
| 5,564,615 A | 10/1996 | Bishop et al. |
| 5,571,090 A | 11/1996 | Sherts |
| 5,573,286 A | 11/1996 | Rogozinski |
| 5,575,799 A | 11/1996 | Bolanos et al. |
| 5,582,617 A | 12/1996 | Klieman et al. |
| 5,591,181 A | 1/1997 | Stone et al. |
| 5,601,224 A | 2/1997 | Bishop et al. |
| 5,620,415 A | 4/1997 | Lucey et al. |
| 5,628,756 A | 5/1997 | Barker, Jr. et al. |
| 5,630,825 A | 5/1997 | de la Torre et al. |
| 5,632,751 A | 5/1997 | Piraka |
| 5,643,293 A | 7/1997 | Kogasaka et al. |
| 5,643,294 A | 7/1997 | Tovey et al. |
| 5,662,666 A | 9/1997 | Onuki et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,690,653 A | 11/1997 | Richardson et al. |
| 5,702,408 A | 12/1997 | Wales et al. |
| 5,715,942 A | 2/1998 | Li et al. |
| 5,728,107 A | 3/1998 | Zlock et al. |
| 5,728,109 A | 3/1998 | Schulze et al. |
| 5,728,113 A | 3/1998 | Sherts |
| 5,730,747 A | 3/1998 | Ek et al. |
| 5,735,874 A | 4/1998 | Measamer et al. |
| 5,746,751 A | 5/1998 | Sherts |
| 5,749,898 A | 5/1998 | Schulze et al. |
| 5,752,973 A | 5/1998 | Kieturakis |
| 5,755,729 A | 5/1998 | de la Torre et al. |
| 5,759,188 A | 6/1998 | Yoon |
| 5,766,196 A | 6/1998 | Griffiths |
| 5,779,646 A | 7/1998 | Koblish et al. |
| 5,792,151 A | 8/1998 | Heck et al. |
| 5,792,153 A | 8/1998 | Swain et al. |
| 5,792,165 A | 8/1998 | Klieman et al. |
| 5,797,537 A | 8/1998 | Oberlin et al. |
| 5,797,927 A | 8/1998 | Yoon |
| 5,797,928 A | 8/1998 | Kogasaka |
| 5,814,054 A | 9/1998 | Kortenbach et al. |
| 5,814,069 A | 9/1998 | Schulze et al. |
| 5,817,119 A | 10/1998 | Klieman et al. |
| 5,827,323 A | 10/1998 | Klieman et al. |
| 5,865,836 A | 2/1999 | Miller |
| 5,871,488 A | 2/1999 | Tovey et al. |
| 5,876,412 A | 3/1999 | Piraka |
| 5,893,592 A | 4/1999 | Schulze et al. |
| 5,897,563 A | 4/1999 | Yoon et al. |
| 5,906,630 A | 5/1999 | Anderhub et al. |
| 5,908,428 A | 6/1999 | Scirica et al. |
| 5,911,727 A | 6/1999 | Taylor |
| 5,928,136 A | 7/1999 | Barry |
| 5,931,855 A | 8/1999 | Buncke |
| 5,938,668 A | 8/1999 | Scirica et al. |
| 5,941,430 A | 8/1999 | Kuwabara |
| 5,947,982 A | 9/1999 | Duran |
| 5,954,731 A | 9/1999 | Yoon |
| 5,954,733 A | 9/1999 | Yoon |
| 5,957,937 A | 9/1999 | Yoon |
| 5,980,538 A | 11/1999 | Fuchs et al. |
| 5,984,932 A | 11/1999 | Yoon |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,017,358 A | 1/2000 | Yoon et al. |
| 6,027,522 A | 2/2000 | Palmer |
| 6,051,006 A | 4/2000 | Shluzas et al. |
| 6,071,289 A | 6/2000 | Stefanchik et al. |
| 6,077,287 A | 6/2000 | Taylor et al. |
| 6,080,180 A | 6/2000 | Yoon et al. |
| 6,086,601 A | 7/2000 | Yoon |
| 6,119,913 A | 9/2000 | Adams et al. |
| 6,126,665 A | 10/2000 | Yoon |
| 6,126,666 A | 10/2000 | Trapp et al. |
| 6,139,563 A | 10/2000 | Cosgrove, III et al. |
| 6,143,004 A | 11/2000 | Davis et al. |
| 6,143,005 A | 11/2000 | Yoon et al. |
| 6,171,316 B1 | 1/2001 | Kovac et al. |
| 6,206,893 B1 | 3/2001 | Klein et al. |
| 6,214,028 B1 | 4/2001 | Yoon et al. |
| 6,223,100 B1 | 4/2001 | Green |
| 6,224,614 B1 | 5/2001 | Yoon |
| 6,261,307 B1 | 7/2001 | Yoon et al. |
| 6,270,508 B1 | 8/2001 | Klieman et al. |
| 6,277,132 B1 | 8/2001 | Brhel |
| 6,319,262 B1 | 11/2001 | Bates et al. |
| 6,332,889 B1 | 12/2001 | Sancoff et al. |
| 6,346,111 B1 | 2/2002 | Gordon et al. |
| 6,358,259 B1 | 3/2002 | Swain et al. |
| 6,494,888 B1 | 12/2002 | Laufer et al. |
| 6,506,196 B1 | 1/2003 | Laufer |
| 6,517,539 B1 | 2/2003 | Smith et al. |
| 6,533,796 B1 | 3/2003 | Sauer et al. |
| 6,569,105 B1 | 5/2003 | Kortenbach et al. |
| 6,582,450 B2 | 6/2003 | Ouchi |
| 6,596,015 B1 | 7/2003 | Pitt et al. |
| 6,599,310 B2 | 7/2003 | Leung et al. |
| 6,638,287 B2 | 10/2003 | Danitz et al. |
| 6,663,639 B1 | 12/2003 | Laufer et al. |
| 6,663,641 B1 | 12/2003 | Kovac et al. |
| 6,666,854 B1 | 12/2003 | Lange |
| 6,676,676 B2 | 1/2004 | Danitz et al. |
| 6,719,764 B1 | 4/2004 | Gellman et al. |
| 6,719,765 B2 | 4/2004 | Bonutti |
| 6,743,239 B1 | 6/2004 | Kuehn et al. |
| 6,743,240 B2 | 6/2004 | Smith et al. |
| 6,755,843 B2 | 6/2004 | Chung et al. |
| 6,773,441 B1 | 8/2004 | Laufer et al. |
| 6,786,913 B1 | 9/2004 | Sancoff et al. |
| 6,821,285 B2 | 11/2004 | Laufer et al. |
| 6,835,200 B2 | 12/2004 | Laufer et al. |
| 6,889,116 B2 | 5/2005 | Jinno |
| 6,936,054 B2 | 8/2005 | Chu |

(56) References Cited

U.S. PATENT DOCUMENTS

| | | |
|---|---|---|
| 6,936,061 B2 | 8/2005 | Sasaki |
| 6,955,643 B2 | 10/2005 | Gellman et al. |
| 6,972,017 B2 | 12/2005 | Smith et al. |
| 6,981,628 B2 | 1/2006 | Wales |
| 6,991,635 B2 | 1/2006 | Takamoto et al. |
| 6,997,931 B2 | 2/2006 | Sauer et al. |
| 7,011,668 B2 | 3/2006 | Sancoff et al. |
| 7,037,315 B2 | 5/2006 | Sancoff et al. |
| 7,041,111 B2 | 5/2006 | Chu |
| 7,052,489 B2 | 5/2006 | Griego et al. |
| RE39,152 E | 6/2006 | Aust et al. |
| 7,063,710 B2 | 6/2006 | Takamoto et al. |
| 7,063,715 B2 | 6/2006 | Onuki et al. |
| 7,107,124 B2 | 9/2006 | Green |
| 7,153,314 B2 | 12/2006 | Laufer et al. |
| 7,191,900 B2 | 3/2007 | Opie et al. |
| 7,192,437 B2 | 3/2007 | Shalaby |
| 7,211,093 B2 | 5/2007 | Sauer et al. |
| 7,218,972 B2 | 5/2007 | Rodriguez |
| 7,232,448 B2 | 6/2007 | Battles et al. |
| 7,244,260 B2 | 7/2007 | Koseki |
| 7,248,944 B2 | 7/2007 | Green |
| 7,364,061 B2 | 4/2008 | Swayze et al. |
| 7,431,189 B2 | 10/2008 | Shelton, IV et al. |
| 7,468,068 B2 | 12/2008 | Kolster |
| 7,601,164 B2 | 10/2009 | Wu |
| 7,645,284 B2 | 1/2010 | Burbank et al. |
| 7,666,194 B2 | 2/2010 | Field et al. |
| 7,691,112 B2 | 4/2010 | Chanduszko et al. |
| 7,704,261 B2 | 4/2010 | Sakamoto et al. |
| 7,708,747 B2 | 5/2010 | Bjerken |
| 7,722,630 B1 | 5/2010 | Stone et al. |
| 7,731,726 B2 | 6/2010 | Belhe et al. |
| 7,736,372 B2 | 6/2010 | Reydel et al. |
| 7,758,597 B1 | 7/2010 | Tran et al. |
| 7,758,598 B2 | 7/2010 | Conlon et al. |
| 7,766,925 B2 | 8/2010 | Stokes et al. |
| 7,771,438 B2 | 8/2010 | Dreyfuss et al. |
| 7,776,059 B2 | 8/2010 | Craig |
| 7,776,066 B2 | 8/2010 | Onuki et al. |
| 7,780,701 B1 | 8/2010 | Meridew et al. |
| 7,784,612 B2 | 8/2010 | Kanda et al. |
| 7,798,325 B2 | 9/2010 | Wizemann et al. |
| 7,814,630 B2 | 10/2010 | Price et al. |
| 7,815,654 B2 | 10/2010 | Chu |
| 7,815,659 B2 | 10/2010 | Conlon et al. |
| 7,828,812 B2 | 11/2010 | Stokes et al. |
| 7,833,235 B2 | 11/2010 | Chu |
| 7,833,237 B2 | 11/2010 | Sauer |
| 7,837,696 B2 | 11/2010 | Modesitt et al. |
| 7,842,047 B2 | 11/2010 | Modesitt et al. |
| 7,842,048 B2 | 11/2010 | Ma |
| 7,846,170 B2 | 12/2010 | Modesitt et al. |
| 7,850,701 B2 | 12/2010 | Modesitt et al. |
| 7,883,517 B2 | 2/2011 | Pantages et al. |
| 7,883,519 B2 | 2/2011 | Oren et al. |
| 7,887,554 B2 | 2/2011 | Stokes et al. |
| 7,905,890 B2 | 3/2011 | Whitfield et al. |
| 7,935,128 B2 | 5/2011 | Rioux et al. |
| 7,947,052 B2 | 5/2011 | Baxter, III et al. |
| 7,947,053 B2 | 5/2011 | McKay et al. |
| 7,951,157 B2 | 5/2011 | Gambale |
| 7,967,832 B2 | 6/2011 | Chu |
| 7,967,842 B2 | 6/2011 | Bakos |
| 7,972,344 B2 | 7/2011 | Murray et al. |
| 7,976,552 B2 | 7/2011 | Suzuki |
| 8,292,906 B2 | 10/2012 | Taylor et al. |
| 8,490,713 B2 | 7/2013 | Furnish et al. |
| 9,615,824 B2 | 4/2017 | Furnish et al. |
| 2002/0010480 A1 | 1/2002 | Sancoff et al. |
| 2002/0065526 A1 | 5/2002 | Oren et al. |
| 2002/0072702 A1 | 6/2002 | Quay |
| 2002/0128666 A1 | 9/2002 | Sancoff et al. |
| 2002/0173800 A1 | 11/2002 | Dreyfuss et al. |
| 2002/0198542 A1 | 12/2002 | Yamamoto et al. |
| 2003/0009195 A1 | 1/2003 | Field et al. |
| 2003/0014077 A1 | 1/2003 | Leung et al. |
| 2003/0045891 A1 | 3/2003 | Yamamoto et al. |
| 2003/0105475 A1 | 6/2003 | Sancoff et al. |
| 2003/0105476 A1 | 6/2003 | Sancoff et al. |
| 2003/0114863 A1 | 6/2003 | Field et al. |
| 2003/0116670 A1 | 6/2003 | Gentry |
| 2003/0171761 A1 | 9/2003 | Sancoff et al. |
| 2003/0233104 A1 | 12/2003 | Gellman et al. |
| 2004/0010245 A1 | 1/2004 | Cerier et al. |
| 2004/0060410 A1 | 4/2004 | Leung et al. |
| 2004/0068272 A1 | 4/2004 | Sauer et al. |
| 2004/0087976 A1 | 5/2004 | DeVries et al. |
| 2004/0092967 A1 | 5/2004 | Sancoff et al. |
| 2004/0181243 A1 | 9/2004 | Chu et al. |
| 2004/0193186 A1 | 9/2004 | Kortenbach et al. |
| 2004/0199184 A1 | 10/2004 | Topper et al. |
| 2005/0043747 A1 | 2/2005 | Field et al. |
| 2005/0085832 A1 | 4/2005 | Sancoff et al. |
| 2005/0096694 A1 | 5/2005 | Lee |
| 2005/0126876 A1 | 6/2005 | Simmons |
| 2005/0165419 A1 | 7/2005 | Sauer et al. |
| 2005/0256533 A1 | 11/2005 | Roth et al. |
| 2006/0025817 A1 | 2/2006 | Ortiz et al. |
| 2006/0036232 A1 | 2/2006 | Primavera et al. |
| 2006/0069396 A1 | 3/2006 | Meade et al. |
| 2006/0111209 A1 | 5/2006 | Hinman et al. |
| 2006/0111732 A1 | 5/2006 | Gibbens et al. |
| 2006/0235304 A1 | 10/2006 | Harhen et al. |
| 2006/0253126 A1 | 11/2006 | Bjerken et al. |
| 2006/0282093 A1 | 12/2006 | Shelton et al. |
| 2007/0005110 A1 | 1/2007 | Collier et al. |
| 2007/0175953 A1 | 8/2007 | Shelton et al. |
| 2008/0082106 A1* | 4/2008 | Doll ............. A61B 17/8875 606/104 |
| 2008/0188868 A1 | 8/2008 | Weitzner et al. |
| 2008/0312688 A1 | 12/2008 | Nawrocki et al. |
| 2009/0054894 A1* | 2/2009 | Yachi ............. A61B 17/320068 606/42 |
| 2009/0259233 A1 | 10/2009 | Bogart et al. |
| 2009/0312773 A1* | 12/2009 | Cabrera ............. A61B 17/0469 606/144 |
| 2010/0010512 A1* | 1/2010 | Taylor ............. A61B 17/04 606/144 |
| 2010/0076260 A1 | 3/2010 | Taylor et al. |
| 2011/0082476 A1 | 4/2011 | Furnish et al. |
| 2012/0215234 A1 | 8/2012 | Chowaniec et al. |

FOREIGN PATENT DOCUMENTS

| | | |
|---|---|---|
| EP | 0647431 A2 | 4/1995 |
| EP | 0836832 A1 | 4/1998 |
| EP | 1481628 A1 | 12/2004 |
| EP | 1915957 A2 | 4/2008 |
| EP | 1915966 A1 | 4/2008 |
| EP | 2044890 A1 | 4/2009 |
| WO | 9811814 A2 | 3/1998 |
| WO | 9811829 A1 | 3/1998 |
| WO | 9853745 A1 | 12/1998 |
| WO | 9915090 A1 | 4/1999 |
| WO | 9918859 A1 | 4/1999 |
| WO | 0067834 A1 | 11/2000 |
| WO | 0174254 A1 | 10/2001 |
| WO | 2002034147 A1 | 5/2002 |
| WO | 03017850 A2 | 3/2003 |
| WO | 03028541 A2 | 4/2003 |
| WO | 2006061868 A1 | 6/2006 |
| WO | 2008042423 A2 | 4/2008 |
| WO | 2008045333 A2 | 4/2008 |
| WO | 2009061504 A1 | 5/2009 |
| WO | 2009132284 A2 | 10/2009 |

OTHER PUBLICATIONS

European Search Report issued in EP 11250290.1 dated Sep. 11, 2014.
Extended European Search Report for EP 07 83 9323 dated Sep. 4, 2014.

(56) References Cited

OTHER PUBLICATIONS

Extended European Search Report corresponding to EP 10 25 1738.0, completed Mar. 13, 2014 and dated Mar. 20, 2014; (5 pp).
International Search Report for PCT/US2007/021506 dated Apr. 16, 2008 (2 pgs.).
European Search Report for EP 07839357.6 dated Nov. 13, 2012 (10 pgs.).
European Search Report for EP 09251544.4 dated Feb. 28, 2013 (18 pgs.).
European Search Report for EP12169361.8 dated Aug. 6, 2012.
International Search Report for PCT/US2007/021447 dated Apr. 8, 2008. (8 pages).
International Search Report for PCT/US2007/021480 date of completion is Feb. 28, 2008 (2 pages).
Extended European Search Report issued in corresponding European Aplication No. 17173431.2 dated Nov. 28, 2017.

* cited by examiner

ENDOSCOPIC STITCHING DEVICE

CROSS-REFERENCE TO RELATED APPLICATIONS

This application claims the benefit of and priority to U.S. Provisional Patent Application No. 62/343,379 filed May 31, 2016, the entire disclosure of which is incorporated by reference herein.

BACKGROUND

Technical Field

The present disclosure relates to devices for suturing or stitching and, more particularly, to devices for endoscopic suturing and/or stitching through an access tube or the like.

Background

One of the advances in recent years to reduce the invasiveness of surgical procedures is endoscopic surgery. Generally, endoscopic surgery involves incising through body walls. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, including those involved in endoscopic surgery, it is often necessary to suture bodily organs or tissue. Suturing may be challenging during endoscopic surgery because of the small openings through which the suturing of bodily organs or tissues must be accomplished. Accordingly, a need exists for simple and effective devices for endoscopic suturing or stitching.

SUMMARY

The present disclosure describes a device for suturing and stitching that demonstrates a practical approach to meeting the performance requirements and overcoming usability challenges associated with endoscopic suturing or stitching. In accordance with an embodiment of the present disclosure, there is provided an endoscopic stitching device including a handle assembly and an elongate shaft assembly. The handle assembly includes a trigger. The elongate shaft assembly includes a hub assembly and an end effector.

The hub assembly includes a main rod operatively associated with the trigger of the handle assembly, a rotatable hub operatively coupled with the main rod such that axial displacement of the main rod rotates the rotatable hub, and first and second arms operatively coupled with the rotatable hub such that rotation of the rotatable hub causes reciprocating axial displacement of the first and second arms. The end effector includes first and second jaws and first and second needle receiving blades slidably dispose in the respective first and second jaws. The first and second jaws are operatively coupled with the main rod of the hub assembly such that axial displacement of the main rod pivots the first and second jaws between open and closed positions.

The first and second needle receiving blades are operatively coupled with the respective first and second arms of the hub assembly such that reciprocating axial displacement of the first and second arms causes reciprocating axial displacement of the first and second needle receiving blades.

In an embodiment, the rotatable hub may define an external cam track configured to slidably engage the first and second arms of the hub assembly therein. The external cam track may define a helical groove. The external cam track may include distal and proximal portions, wherein at least one of the distal or proximal portions may extend transverse to a longitudinal axis defined by the rotatable hub.

In yet another embodiment, the rotatable hub may further define an internal cam path in an inner surface thereof. The internal cam path may define a pair of spaced apart helical grooves and a pair of opposed axially oriented grooves interconnecting the helical grooves.

In yet another embodiment, the first and second arms of the hub assembly may diametrically oppose each other.

In still yet another embodiment, the main rod may include a camming pin extending transversely outward. The camming pin may be configured to slide through the internal cam path of the rotatable hub to cause rotation of the rotatable hub.

In another embodiment, the handle assembly may include a driver plunger operatively associated with the main rod of the hub assembly, wherein actuation of the trigger may advance the drive plunger distally.

In still another embodiment, the main rod may be movable between a proximal position in which the camming pin is proximal of the rotatable hub and a distal position in which the camming pin is received within the internal cam path. The main rod may be biased toward the proximal position.

In accordance with another embodiment of the present disclosure, there is provided an elongate shaft assembly for use with an endoscopic stitching device. The elongate shaft assembly includes a hub assembly and an end effector. The hub assembly includes an insertion portion and an engaging portion. The insertion portion is configured to be received in a handle assembly of the endoscopic stitching device. The insertion portion includes a main rod, a rotatable hub operatively coupled with the main rod such that axial displacement of the main rod rotates the rotatable hub, and first and second arms operatively coupled with the rotatable hub such that rotation of the rotatable hub causes reciprocating axial displacement of the first and second arms. The engaging portion is movable relative to the insertion portion between a reload position in which the rotatable hub is in a distal-most position and rotatable independent of axial displacement of the main rod, and a loaded position in which axial displacement of the main rod rotates the rotatable hub.

The end effector includes first and second jaws operatively coupled with the main rod such that axial displacement of the main rod pivots the first and second jaws between open and closed positions and first and second needle receiving blades slidably disposed in the respective first and second jaws. The first and second needle receiving blades are operatively coupled with the respective first and second arms of the hub assembly such that reciprocating axial displacement of the first and second arms causes reciprocating axial displacement of the first and second needle receiving blades.

In an embodiment, the engaging portion of the hub assembly may be biased toward the reload position.

In another embodiment, the hub assembly may further include a latch to selectively secure the engaging portion to the reload or loaded position. The insertion portion may define a locking groove to secure the latch therein. The rotatable hub may define a locking recess to secure the latch therein.

DETAILED DESCRIPTION OF THE DRAWINGS

The foregoing objects, features and advantages of the disclosure will become more apparent from a reading of the following description in connection with the accompanying drawings, in which.

DETAILED DESCRIPTION

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Figure 1:
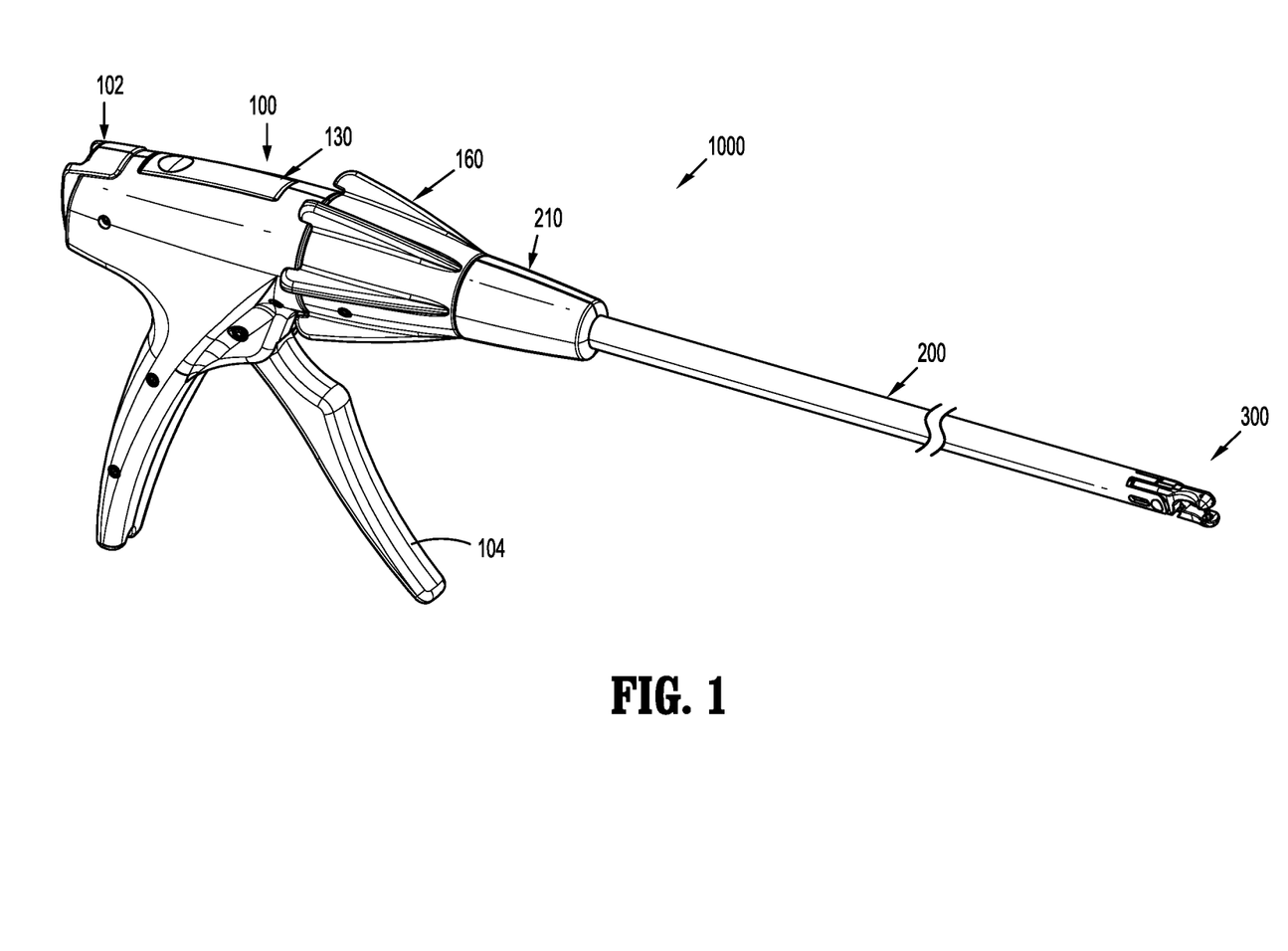
FIG. 1 is a perspective view of a stitching device in accordance with an embodiment of the present disclosure.

With reference to FIG. 1, an embodiment of the present disclosure is generally shown as a stitching device 1000. Stitching device 1000 is adapted to be particularly useful in endoscopic or laparoscopic procedures, wherein an endoscopic portion of stitching device 1000 such as, e.g., an end effector 300, is insertable into an operative site, via a cannula assembly or the like (not shown). Stitching device 1000 includes a handle assembly 100 and an elongate shaft assembly 200 extending distally from handle assembly 100. Handle assembly 100 and elongate shaft assembly 200 may be detachably coupled, as will be described hereinbelow. Such a configuration facilitates, e.g., sterilization of stitching device 1000 and interchangeability of end effector 300.

Figure 2:
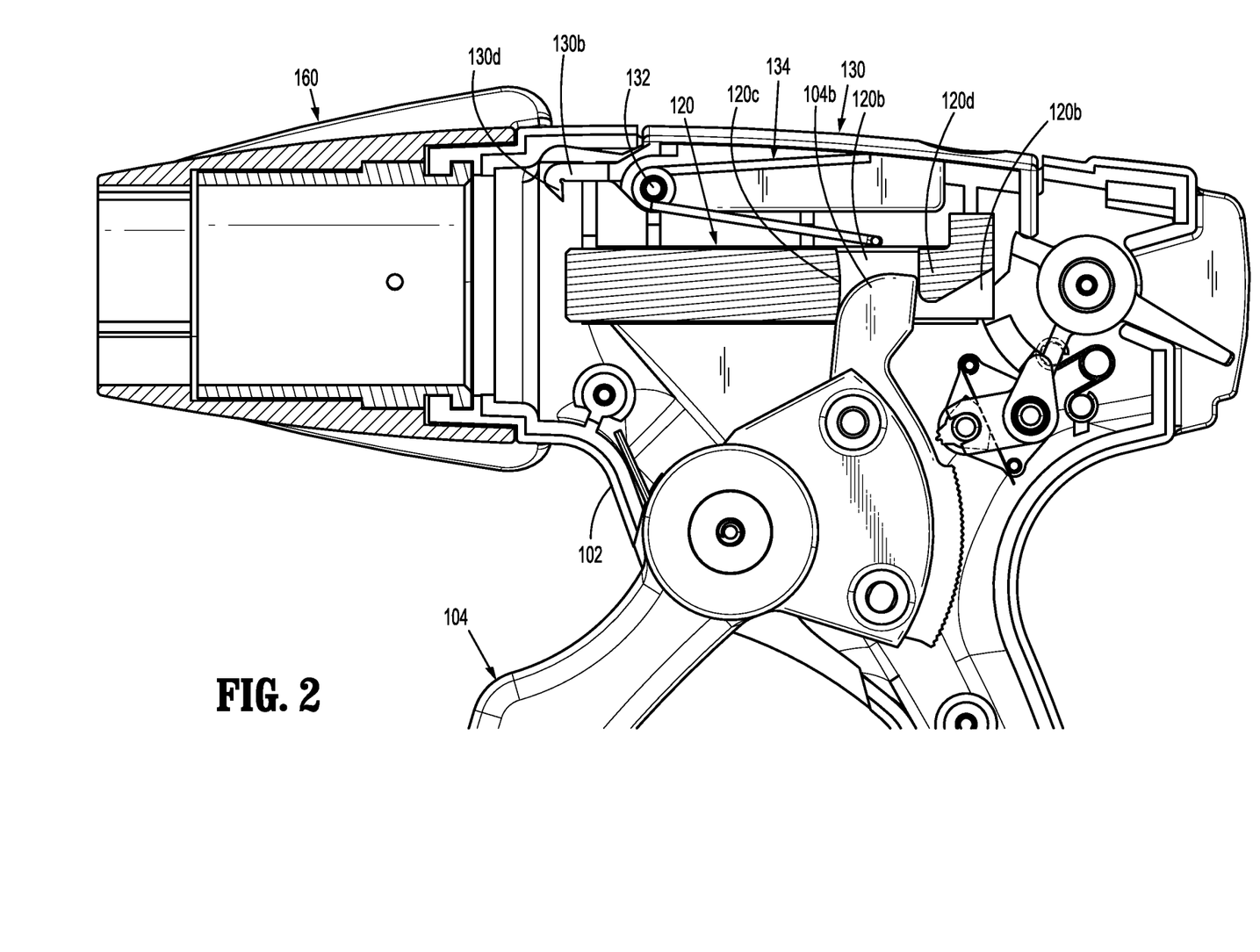
FIG. 2 is a cross-sectional view of a handle assembly of the stitching device of FIG. 1.

With reference to FIGS. 1 and 2, handle assembly 100 includes a trigger 104 pivotably supported on a housing 102 and a drive plunger 120 operatively connected to trigger 104. Drive plunger 120 is slidably supported within housing 102. Drive plunger 120 defines a proximally extending trigger slot 120b formed in a proximal portion thereof to operatively receive drive arm 104b of trigger 104. Trigger slot 120b defines a distal surface or wall 120c against which a distal surface of drive arm 104b of trigger 104 contacts in order to distally advance drive plunger 120 during actuation of trigger 104.

Handle assembly 100 further includes an endoscopic assembly release lever 130 pivotally supported on and connected to housing 102 via a pivot pin 132. Release lever 130 includes a distal end 130b extending distally of pivot pin 132. Distal end 130b of release lever 130 includes a catch or tooth 130d projecting therefrom, in a direction towards drive plunger 120. Catch 130d may be located distal of drive plunger 120. A biasing member 134, in the form of, e.g., a leaf spring, may be provided to bias catch 130d towards drive plunger 120. Biasing member 134 maintains catch 130d of release lever 130 in engagement with an annular recess 212c (FIG. 3) of endoscopic assembly 200. Handle assembly 100 may further include a rotation knob 160 rotatably supported on housing 102 to enable concomitant rotation of end effector 300. Reference may be made to U.S. Pat. No. 7,905,890, entitled "Endoscopic Surgical Clip Applier," or U.S. Provisional Patent Application Ser. No. 62/253,162, filed on Nov. 10, 2015, entitled "Endoscopic Reposable Surgical Clip Applier," the entire content of each of which is incorporated herein by reference, for a detailed discussed of the construction and operation of a handle assembly.

Figure 3:
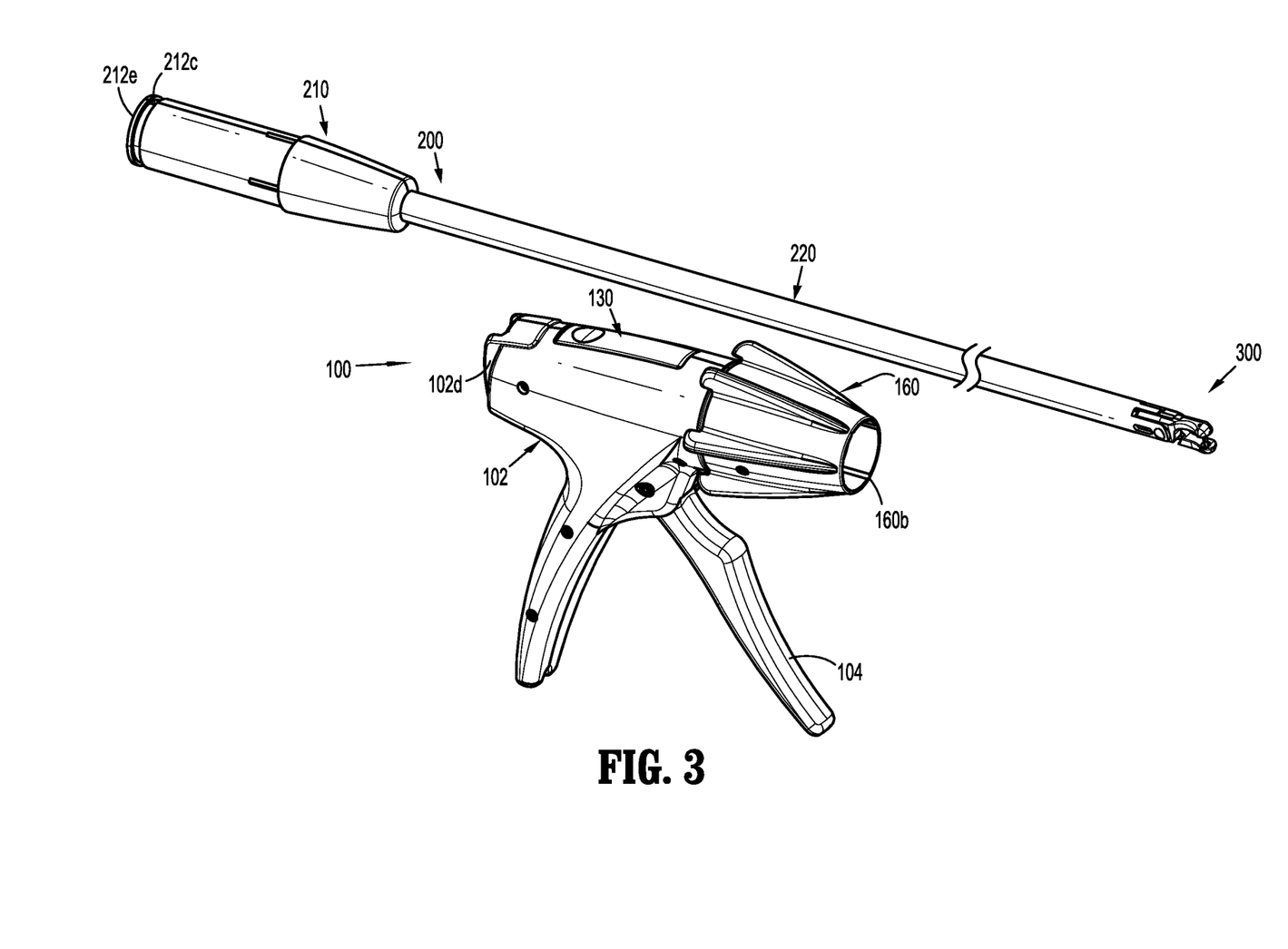
FIG. 3 is a perspective view of the stitching device of FIG. 1, illustrating detachability of the handle assembly and an elongate shaft assembly.
Figure 4:
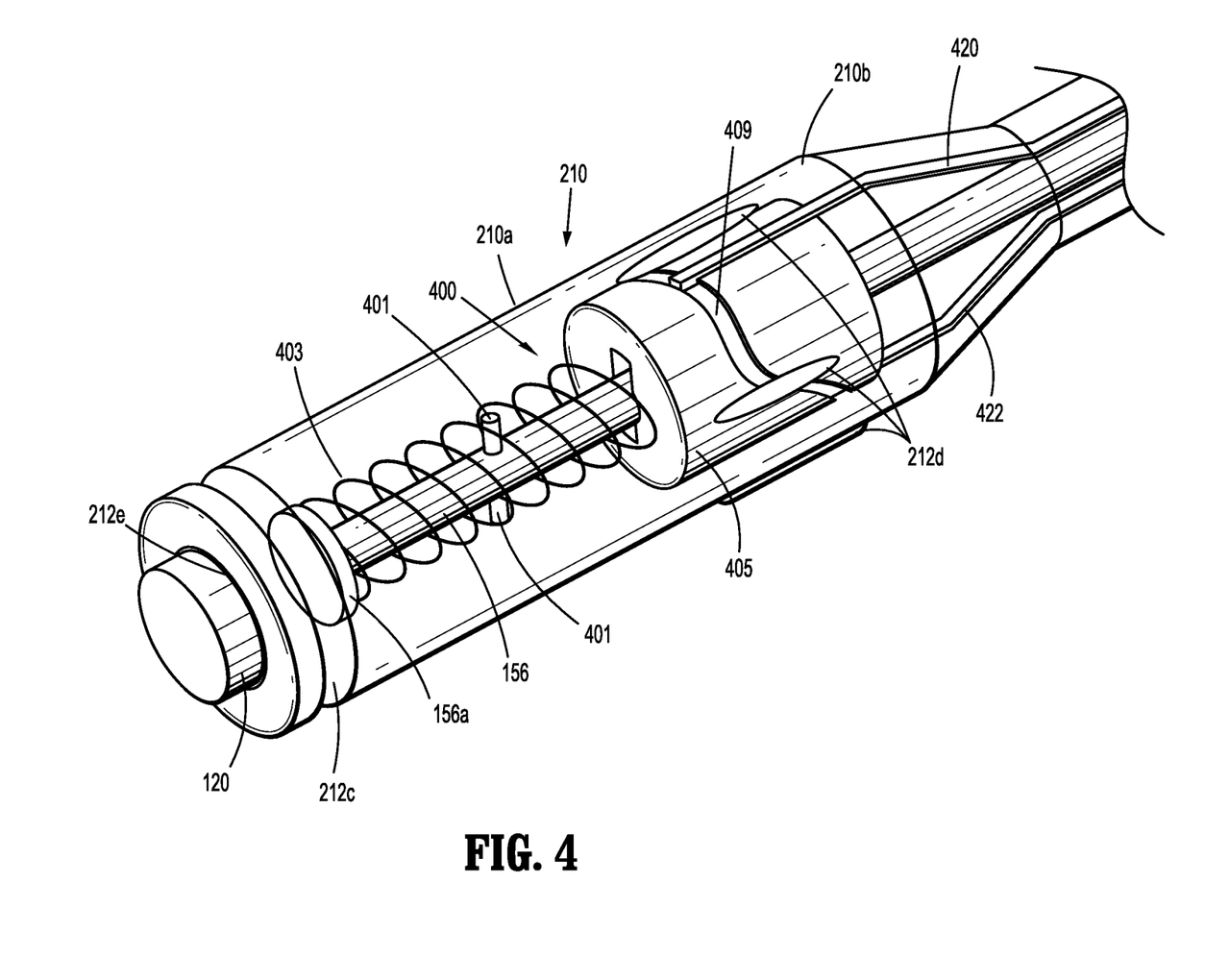
FIG. 4 is a perspective view of a hub assembly of the elongate shaft assembly of FIG. 3.

With reference to FIGS. 3 and 4, elongate shaft assembly 200 is detachable from handle assembly 100. Elongate shaft assembly 200 includes a hub assembly 210, an elongate shaft 220, and an end effector 300 operably coupled with trigger 104 of handle assembly 100. Hub assembly 210 serves as an adapter assembly for a selective connection to rotation knob 160 of handle assembly 100. Hub assembly 210 includes an insertion portion 210a and an engaging portion 210b extending distally from insertion portion 210a. Insertion portion 210a is configured to be received within handle assembly 100. Engaging portion 210b is disposed adjacent rotation knob 160 when insertion portion 210a is secured with handle assembly 100.

Insertion portion 210a may define an annular recess 212c configured to detachably receive catch 130d (FIG. 2) of release lever 130 to secure elongate shaft assembly 200 with handle assembly 100. In addition, insertion portion 210a includes circumferentially arranged ribs 212d (FIG. 4). Complementary grooves 160b (FIG. 3) are defined in rotation knob 160 of handle assembly 100 such that ribs 212d are slidably received in respective grooves 160b of rotation knob 160 of handle assembly 100 during connection of elongate shaft assembly 200 and handle assembly 100. The connection of hub assembly 210 of elongate shaft assembly 200 with rotation knob 160 of handle assembly 100 enables elongate shaft assembly 200 to rotate about a longitudinal axis thereof, relative to handle assembly 100.

Figure 5:
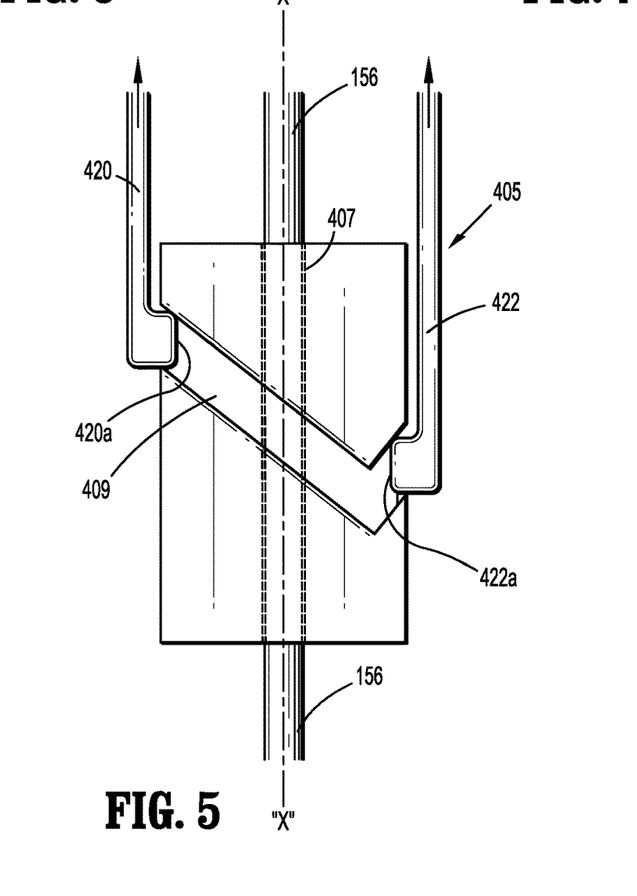
FIG. 5 is a top view of a rotatable hub of the hub assembly of FIG. 4.

With respect to FIGS. 4 and 5, insertion portion 210a of hub assembly 210 includes a drive conversion assembly 400 configured to convert axial displacement of drive plunger 120 of handle assembly 100 into rotation of a rotatable hub 405 in order to provide an axial output of main rod 156 and axial outputs of reciprocating first and second arms 420, 422 in opposite directions. Main rod 156 is operatively coupled to jaws 130, 132 of end effector 300, and rotatable hub 405, namely first and second arms 420, 422, is operatively coupled to a pair of needle engaging members or blades 150, 152 (FIG. 9) of end effector 300, as will be discussed hereinbelow.

Hub assembly 210 defines a proximal opening 212e configured to slidably receive drive plunger 120 of handle assembly 100, when elongate shaft assembly 200 is coupled to handle assembly 100. Main rod 156 includes a proximal end 156a configured to engage drive plunger 120 of handle assembly 100 and a distal end (not shown) connected to jaws 130, 132 (FIG. 9) of end effector 300. Main rod 156 includes a camming pin 401 extending transversely outward. A biasing member 403 such as, e.g., a compression spring, is interposed between proximal end 156a of main rod 156 and rotatable hub 405 such that main rod 156 is biased toward an initial position.

With continued reference now to FIGS. 4 and 5, rotatable hub 405 is configured for rotatable disposition within hub assembly 210. Rotatable hub 405 defines a lumen 407 configured to slidably receive main rod 156 therethrough. Rotatable hub 405 defines an external cam track 409 (FIG. 5) in a form of, e.g., helical or spiral groove, in an outer surface thereof and an internal cam path 411 (FIG. 6) on an inner surface thereof.

Figure 6:
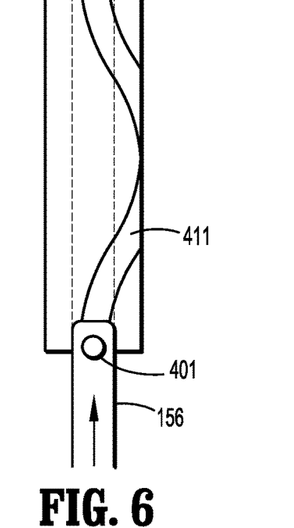
FIG. 6 is a cross-sectional view of an inner surface of the rotatable hub of FIG. 4, illustrating an internal cam path thereof.
Figure 7:
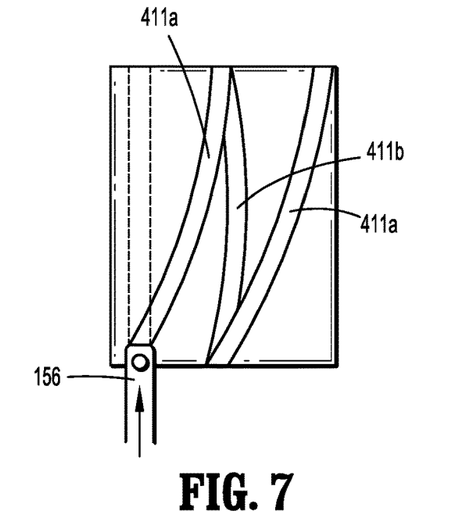
FIG. 7 is a schematic view of the inner surface of the rotatable hub of FIG. 4, illustrating the internal cam path thereof.

With reference to FIGS. 5-7, distal and proximal ends of external cam track 409 may extend transverse to a longitudinal axis "X-X" (FIG. 5) of rotatable hub 405. Internal cam path 411 defines a pair of spaced apart helical grooves 411a formed in the inner surface of rotatable hub 405 (FIG. 5) and a pair of opposed axially oriented grooves 411b formed in the inner surface of rotatable hub 405 and interconnecting helical grooves 411a.

Figure 8:
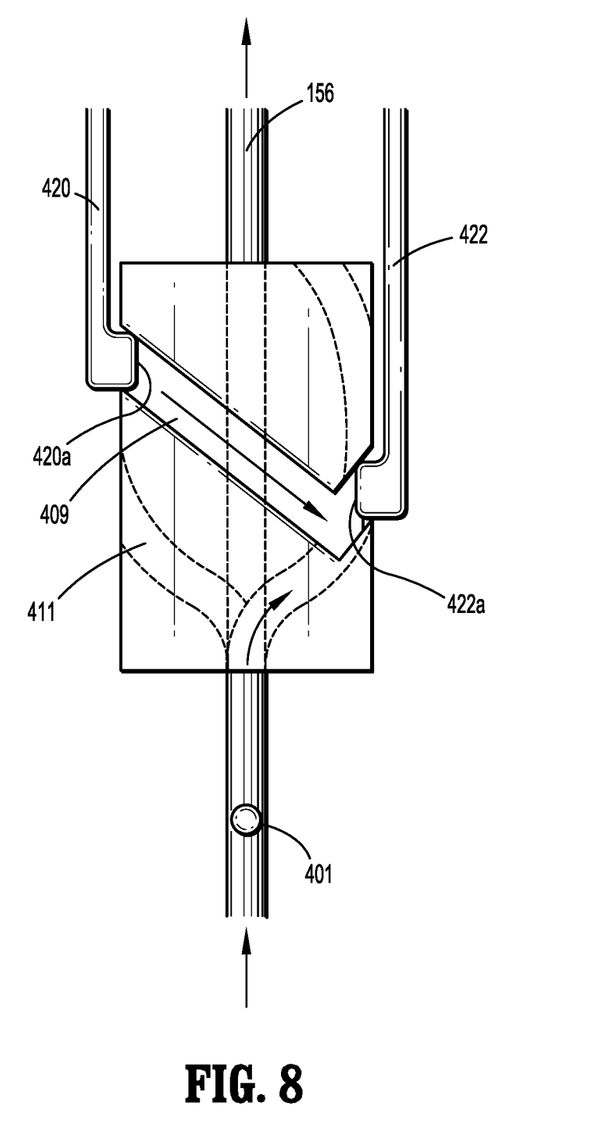
FIG. 8 is a top view of the rotatable hub of FIG. 5, illustrating the internal cam path in phantom.

With reference to FIG. 8, hub assembly 210 further includes first and second arms 420, 422 operatively coupled with blades 150, 152 (FIG. 9) of end effector 300. First and second arms 420, 422 diametrically oppose each other. First and second arms 420, 422 include respective bosses 420a, 422a slidably received in external cam track 409 of rotatable hub 405. Camming pin 401 extending transversely from main rod 156 is dimensioned for slidable engagement in internal cam path 411 of rotatable hub 405. Under such a configuration, when main rod 156 is advanced distally jaws 130, 132 transition to the closed position, and camming pin 401 slidably engages internal cam path 411, which, in turn, rotates rotatable hub 405. As rotatable hub 405 is rotated, respective bosses 420a, 422a of first and second arms 420, 422 ride within external cam track 409 of rotatable hub 405 and are displaced axially in opposite directions. Axial displacement of first and second arms 420, 422 in opposite directions causes reciprocating motions of blades 150, 152 (FIG. 9) of end effector 300. In this manner, single actuation of trigger 104 causes both axial displacement of main rod 156 and reciprocating displacement of first and second arms 420, 422, which effects opening and closing of jaws 130, 132 and reciprocating axial displacement of blades 150, 152, respectively.

Figure 9:
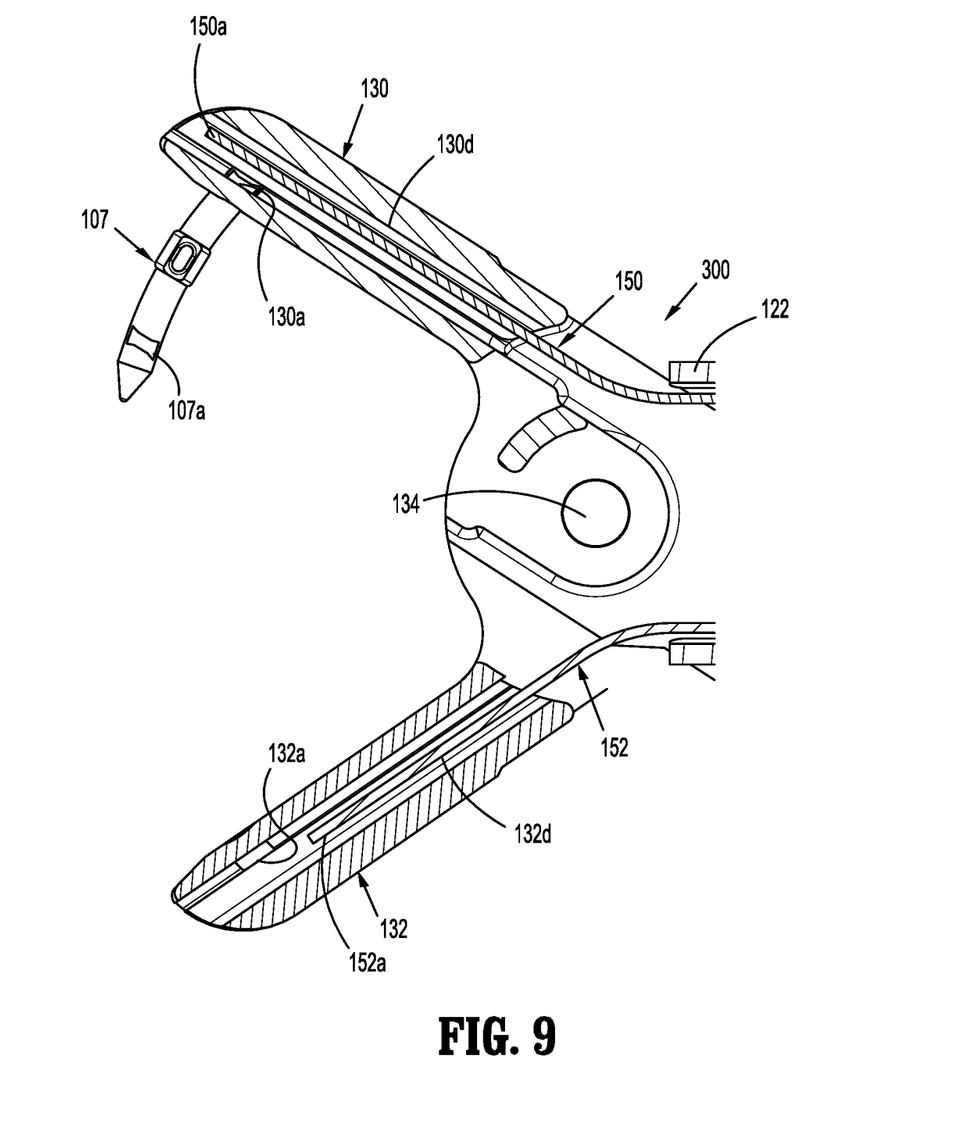
FIG. 9 is a partial cross-sectional view of an end effector of the elongate shaft assembly of FIG. 1.
Figure 10:
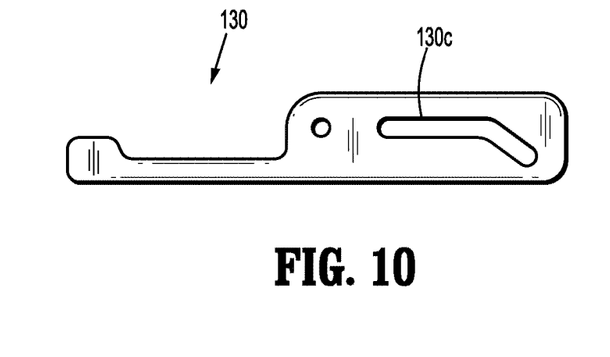
FIG. 10 is a side view of a jaw member for use with the end effector of FIG. 9.

With reference to FIG. 9, elongate shaft assembly 200 includes end effector 300. End effector 300 includes a support member 122 and jaws 130, 132 pivotably mounted on support member 122 by means of a jaw pivot pin 134. To move jaws 130, 132 between open and closed positions, main rod 156 has a camming pin (not shown) mounted at a distal end 156a thereof. Camming pin 138 rides in angled camming slots 130c (FIG. 10) defined in respective jaws 130, 132 such that axial or longitudinal movement of main rod 156 causes jaws 130, 132 to be cammed between the open and closed positions. For example, when main rod 156 is advanced distally, jaws 130, 132 transition to the closed position.

End effector 300 further includes a pair of needle engaging members or blades 150, 152 that are slidably supported within support member 122. Each blade 150, 152 includes a distal end 150a, 152a slidably extending into blade receiving channels 130d, 132d of respective jaws 130, 132. Channels 130d, 132d are dimensioned to at least partially intersect needle recesses 130a, 132a. Thus, by advancing blade 150 or 152 within respective channel 130d, 132d, distal end 150a, 152a of advancing blade 150, 152 engages or "locks in" a groove 107a formed in needle 107 when at least a portion of needle 107 is received within respective needle recesses 130a, 132a. A suture (not shown) may be secured to needle 107. The suture may include a plurality of barbs oriented to resist movement in a direction opposite to the direction of travel.

With respect to FIGS. 3 and 4, in use, insertion portion 210a of hub assembly 210 is received in handle assembly 100 such that catch 130d (FIG. 2) of release lever 130 securely engages annular recess 212c defined in insertion portion 210a of hub assembly 210. At this time, a portion of drive plunger 120 is received through proximal opening 212e of hub assembly 210.

With reference to FIG. 9, initially, notches (not shown) formed in respective blades 150, 152 are aligned with or in registration with respective needle recesses 130a, 132a defined in respective jaws 130, 132. With the notches of blades 150, 152 aligned with or in registration with the respective needle recesses 130a, 132a of respective jaws 130, 132, needle 107 may be positioned or loaded into a selected one needle recess 130a, 132a of jaws 130, 132.

Once needle 107 is loaded into one of the needle recess 130a, 132a of jaws 130, 132, trigger 104 is actuated to rotate rotatable hub 405, which, in turn, causes reciprocating axial displacement of first and second arms 420, 422 (FIG. 4) so that only one blade 150, 152, is in engagement with needle 107, and the other blade 150, 152 is disengaged from needle 107. With only one blade 150, 152 engaged with needle 10, trigger 104 may be released, thereby moving main rod 156 proximally to open jaws 130, 132.

With jaws 130, 132 in the open position and needle 107 loaded and held in one jaw 130 or 132, jaws 130, 132 may be positioned about or over a target tissue and handles 110 may be actuated to approximate jaws 130, 132. As jaws 130, 132 are approximated, the exposed end of needle 107 is penetrated through the target tissue and enters opposed jaw 130 or 132. With needle 107 in opposed jaw 130 or 132, as main rod 156 is further advanced blades 150, 152 are reversed. In so doing, needle 107 is swapped from one blade 150 or 152 to the other blade 150 or 152, and thus, loaded or held in the other jaw 130 or 132.

With needle 107 being swapped from one blade 150, 152 to another blade 150, 152, trigger 104 may be released to thereby open jaws 130, 132 and draw needle 107 through the target tissue. In so doing, the suture is also drawn through the tissue. The process is repeated, passing needle 107 between jaws 130, 132 and drawing the suture through the target tissue, thereby suturing the target tissue as needed or desired.

Figure 11:
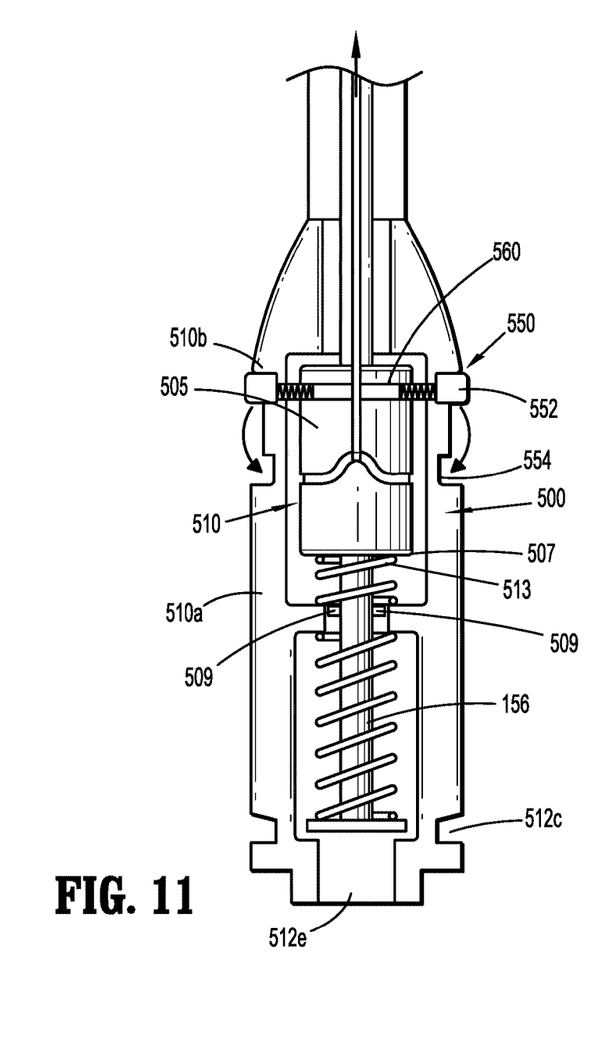
FIG. 11 is a top view of a hub assembly for use with the stitching device of FIG. 1 in accordance with an embodiment of the present disclosure.

With reference now to FIG. 11, there is illustrated a hub assembly 510 in accordance with another embodiment of the present disclosure. Hub assembly 510 includes features that are identical to the features described with respect to hub assembly 210. Thus, the identical parts in hub assembly 510 will not be described herein to avoid obscuring the present disclosure in unnecessary detail.

Hub assembly 510 includes an insertion portion 510a and an engaging portion 510b distal of insertion portion 510a. Insertion portion 510a is configured to be received within handle assembly 100. When coupled with handle assembly 100, engaging portion 510b is disposed adjacent rotation knob 160 (FIG. 3). Hub assembly 510 further includes a reload mechanism 550 configured to transition blades 150, 152 (FIG. 9) of end effector 300 to a reload mode. In the reload mode, each blade 150, 152 of respective jaws 130, 132 is in a distal-most position. In this manner, notches (not shown) formed in respective blades 150, 152 are aligned with or in registration with respective needle recesses 130a, 132a defined in respective jaws 130, 132. With the notches of blades 150, 152 aligned with or in registration with the respective needle recesses 130a, 132a of respective jaws 130, 132, needle 107 (FIG. 2) may be positioned or loaded into a selected one needle recess 130a, 132a of jaws 130, 132.

Engaging portion 510b is movable relative to insertion portion 510a. Reload mechanism 550 includes a latch 552 configured to be received in a locking recess 560 rotatable hub 505 or a locking groove 554 defined in insertion portion 510a, whereby engaging portion 550b is transitionable between a reload position in which latch 552 is received in locking recess 560 defined in rotatable hub 505 and a loaded position in which engaging portion 510b is pulled proximally such that latch 552 is received in locking groove 554 of insertion portion 510a. When latch 552 is received in a locking recess 560 defined in rotatable hub 505, relative rotation between engaging portion 510b and rotatable hub 505 may be inhibited.

In the reload position, rotatable hub 505 is in a distal-most position. At this time, camming pin 509 on main rod 156 is disposed proximal of rotatable hub 505 or an internal cam path (not shown) defined in an inner surface of rotatable hub 505 such that rotatable hub 505 is rotatable independent of axial displacement of main rod 156. Rotatable hub 505 positioned in the distal-most position enables blades 150, 152 (FIG. 2) of respective jaws 130, 132 to be in the distal-most position, which, in turn, enables loading of needle 107 into a selected one needle recess 130a, 132a of jaws 130, 132. In the loaded position, camming pin 509 is disposed in the internal cam path of rotatable hub 505, whereby axial displacement of main rod 156 causes transition of jaws 130, 132 between the open and closed positions and reciprocating axial displacement of blades 150, 152 in opposite directions. Hub assembly 510 may further include a biasing member 513 such as, e.g., a compression spring, to bias rotatable hub 505 toward the reload position.

Insertion portion 510a of hub assembly 510 includes a drive conversion assembly 500 configured to convert axial displacement drive plunger 120 of handle assembly 100 into axial displacement of a main rod 156 and rotation of a rotatable hub 505. Main rod 156 is operatively coupled to jaws 130, 132 of end effector 300, and rotatable hub 505 is operatively coupled to blades 150, 152 (FIG. 9) of end effector 300.

In use, stitching device 1000 is first transitioned to the reload mode by releasing latch 552 and sliding engaging portion 510b distally such that both blades 150, 152 (FIG. 9) are in the distal-most position. In this manner, notches (not shown) formed in respective blades 150, 152 are aligned with or in registration with respective needle recesses 130a, 132a defined in respective jaws 130, 132. With the notches of blades 150, 152 aligned with or in registration with the respective needle recesses 130a, 132a of respective jaws 130, 132, needle 107 (FIG. 9) may be positioned or loaded into a selected one needle recess 130a, 132a of jaws 130, 132.

At this time, insertion portion 510a of hub assembly 510 is received in handle assembly 100 such that catch 130d of release lever 130 securely engages annular recess 512c defined insertion portion 510a of hub assembly 510. At this time, a portion of drive plunger 120 is received in a proximal opening 512e of hub assembly 510.

At this time, trigger 104 (FIG. 1) may be squeezed to cause axial displacement of main rod 156, which, in turn, transitions jaws 130, 132 to the closed position, and rotates rotatable hub 505 so that only one blade 150, 152 is in engagement with needle 107 (FIG. 2), and the other blade 150, 152 is disengaged from needle 107. When trigger 104 is released, main rod 156 is displaced proximally, which, in turn, opens jaws 130, 132.

With jaws 130, 132 in the open position and needle 107 loaded and held in one jaw 130 or 132, jaws 130, 132 may be positioned about or over a target tissue and trigger 104 may be actuated to approximate jaws 130, 132. As jaws 130, 132 are approximated, the exposed end of needle 107 is penetrated through the target tissue and enters opposed jaw 130 or 132. With needle 107 in opposed jaw 130 or 132, lever 182 is once again actuated or rotated so that blades 150, 152 are reversed. In so doing, needle 107 is swapped from one blade 150 or 152 to the other blade 150 or 152, and thus, loaded or held in the other jaw 130 or 132.

With needle 107 being swapped from one blade 150, 152 to another blade 150, 152, handles 110 may be released to thereby open jaws 130, 132 and draw needle 107 through the target tissue. In so doing, the suture is also drawn through the tissue. The process is repeated, passing needle 107 between jaws 130, 132 and drawing the suture through the target tissue, thereby suturing the target tissue as needed or desired.

Although the illustrative embodiments of the present disclosure have been described herein with reference to the accompanying drawings, the above description, disclosure, and figures should not be construed as limiting, but merely as exemplifications of particular embodiments. For example, elongate shaft assembly 200 may include an articulable section to facilitate maneuverability of stitching device through the anatomical structure of the patient. It is to be understood, therefore, that the disclosure is not limited to those precise embodiments, and that various other changes and modifications may be effected therein by one skilled in the art without departing from the scope or spirit of the disclosure.

What is claimed is:

1. An endoscopic stitching device, comprising:
a handle assembly including a trigger; and
an elongate shaft assembly including:
  a hub assembly including:
    a main rod operatively associated with the trigger of the handle assembly, the main rod including a camming pin extending transversely outward;
    a rotatable hub operatively coupled with the main rod such that axial displacement of the main rod rotates the rotatable hub; and
    first and second arms operatively coupled with the rotatable hub such that rotation of the rotatable hub causes reciprocating axial displacement of the first and second arms; and
  an end effector including:

first and second jaws operatively coupled with the main rod of the hub assembly such that axial displacement of the main rod between a first state in which the camming pin of the main rod is disposed externally of the rotatable hub and the rotatable hub is rotatable independent of axial displacement of the main rod, and a second state in which the camming pin is disposed within the rotatable hub, pivots the first and second jaws between open and closed positions; and first and second needle receiving blades slidably disposed in the respective first and second jaws, the first and second needle receiving blades operatively coupled with the respective first and second arms of the hub assembly such that reciprocating axial displacement of the first and second arms causes reciprocating axial displacement of the first and second needle receiving blades which allows a needle to be swapped from one of the first and second needle receiving blades to the other of the first and second needle receiving blades thereby allowing target tissue to be stitched.

2. The endoscopic stitching device according to claim 1, wherein the rotatable hub defines an external cam track configured to slidably engage the first and second arms of the hub assembly therein.

3. The endoscopic stitching device according to claim 2, wherein the external cam track defines a helical groove.

4. The endoscopic stitching device according to claim 3, wherein the external cam track includes distal and proximal portions, at least one of the distal or proximal portions extending transverse to a longitudinal axis defined by the rotatable hub.

5. The endoscopic stitching device according to claim 2, wherein the rotatable hub further defines an internal cam path in an inner surface thereof.

6. The endoscopic stitching device according to claim 5, wherein the camming pin is configured to slide through the internal cam path of the rotatable hub to cause rotation of the rotatable hub.

7. The endoscopic stitching device according to claim 6, wherein the main rod is movable between a proximal position in which the camming pin is proximal of the rotatable hub and a distal position in which the camming pin is received within the internal cam path.

8. The endoscopic stitching device according to claim 7, wherein the main rod is biased toward the proximal position.

9. The endoscopic stitching device according to claim 5, wherein the internal cam path defines a pair of spaced apart helical grooves and a pair of opposed axially oriented grooves interconnecting the helical grooves.

10. The endoscopic stitching device according to claim 2, wherein the handle assembly further includes a driver plunger operatively associated with the main rod of the hub assembly, wherein actuation of the trigger advances the drive plunger distally.

11. The endoscopic stitching device according to claim 1, wherein the first and second arms of the hub assembly diametrically oppose each other.

12. An elongate shaft assembly for use with an endoscopic stitching device, comprising:
a hub assembly including:
an insertion portion configured to be received in a handle assembly of the endoscopic stitching device, the insertion portion including:
a main rod including a camming pin extending transversely outward;

a rotatable hub operatively coupled with the main rod such that axial displacement of the main rod rotates the rotatable hub; and first and second arms operatively coupled with the rotatable hub such that rotation of the rotatable hub causes reciprocating axial displacement of the first and second arms; and an engaging portion movable relative to the insertion portion between a reload position in which the rotatable hub is in a distal-most position and rotatable independent of axial displacement of the main rod, and a loaded position in which axial displacement of the main rod rotates the rotatable hub; and an end effector including:
first and second jaws operatively coupled with the main rod such that axial displacement of the main rod between a first state in which the camming pin of the main rod is disposed externally of the rotatable hub and a second state in which the camming pin is disposed within the rotatable hub pivots the first and second jaws between open and closed positions; and first and second needle receiving blades slidably disposed in the respective first and second jaws, the first and second needle receiving blades operatively coupled with the respective first and second arms of the hub assembly such that reciprocating axial displacement of the first and second arms causes reciprocating axial displacement of the first and second needle receiving blades which allows a needle to be swapped from one of the first and second needle receiving blades to the other of the first and second needle receiving blades thereby allowing target tissue to be stitched.

13. The elongate shaft assembly according to claim 12, wherein the engaging portion of the hub assembly is biased toward the reload position.

14. The elongate shaft assembly according to claim 13, wherein the rotatable hub defines an external cam track configured to slidably engage the first and second arms of the hub assembly therein.

15. The elongate shaft assembly according to claim 14, wherein the rotatable hub further defines an internal cam path in an inner surface thereof.

16. The elongate shaft assembly according to claim 15, wherein the camming pin is configured to slide through the internal cam path of the rotatable hub to cause rotation of the rotatable hub.

17. The elongate shaft assembly according to claim 16, wherein the main rod is movable between a proximal position in which the camming pin is proximal of the rotatable hub and a distal position in which the camming pin is engaged within the internal cam path.

18. The elongate shaft assembly according to claim 17, wherein the main rod is biased toward the proximal position.

19. The elongate shaft assembly according to claim 12, wherein the hub assembly further includes a latch to selectively secure the engaging portion to the reload or loaded position.

20. The elongate shaft assembly according to claim 19, wherein the insertion portion defines a locking groove to secure the latch therein.

21. The elongate shaft assembly according to claim 19, wherein the rotatable hub defines a locking recess to secure the latch therein.

22. The elongate shaft assembly according to claim 12, wherein the first and second jaws of the end effector are operatively coupled with the main rod such that distal displacement of the main rod approximates the first and second jaws.

* * * * *